United States Patent
Tsujii (10) Patent No.: US 7,056,021 B2
(45) Date of Patent: Jun. 6, 2006

(54) RADIOGRAPHIC APPARATUS AND WATER CALIBRATION METHOD

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 10/858,249

(22) Filed: Jun. 1, 2004

(65) Prior Publication Data

US 2004/0252810 A1    Dec. 16, 2004

(30) Foreign Application Priority Data

Jun. 10, 2003    (JP)    ............... 2003-165030

(51) Int. Cl.
G21D 18/00    (2006.01)
G21K 1/12    (2006.01)
A61B 6/00    (2006.01)

(52) U.S. Cl. ................... 378/207; 378/18; 378/19
(58) Field of Classification Search ............. 378/18, 378/19, 20, 4, 207, 205; 382/132
See application file for complete search history.

(56) References Cited

U.S. PATENT DOCUMENTS 6,041,097 A * 3/2000 Roos et al. ............... 378/62
6,470,068 B1 * 10/2002 Cheng ..................... 378/20
6,848,827 B1 * 2/2005 Wu et al. ................ 378/207

FOREIGN PATENT DOCUMENTS

JP    2000-107162    4/2000
JP    2000-217810    8/2000

* cited by examiner

*Primary Examiner*—Edward J. Glick
*Assistant Examiner*—Irakli Kiknadze
(74) *Attorney, Agent, or Firm*—Morgan & Finnegan LLP (57) ABSTRACT

A radiographic apparatus has a radiation source that emits radiation two-dimensionally, a two-dimensional radiation detector disposed so as to detect radiation emitted from the radiation source, a rotation unit driven so that a subject is relatively rotated with respect to said radiation source and said radiation detector, a detachable water phantom, disposed on the rotation unit, having a size that covers a portion of a detection area of the radiation detector from radiation emitted from the radiation source, the portion extending in the direction perpendicular to the rotation axis for the entire range of the detection area and in the direction of the rotation axis for a part of the range of the detection area, and a calibration unit that performs water calibration of data obtained by radiography of the subject, using data obtained by radiography of the water phantom across the entire detection area while moving a position of the water phantom along the axis rotation of the rotation unit.

8 Claims, 9 Drawing Sheets

RADIOGRAPHIC APPARATUS AND WATER CALIBRATION METHOD

FIELD OF THE INVENTION

The present invention relates to a radiographic apparatus that uses ordinary radiation of an X-ray CT apparatus that senses an image using radiation such as X-rays to sense a radiographic characteristics distribution inside a subject, and more particularly, to water calibration in a cone beam CT apparatus.

BACKGROUND OF THE INVENTION

Conventionally, a Computerized Tomography (hereinafter "CT") X-ray apparatus is known that irradiate a subject with X-rays, detects X-rays passing through the subject or dispersed by a subject with an X-ray detector and creates either a transparent image, a tomographic image or a three-dimensional image based on the output of the X-ray detector (that is, the amount of X-rays).

A so-called cone beam CT apparatus has been developed as one type of such X-ray CT apparatus. In an ordinary X-ray CT apparatus, the X-ray beam is sliced thinly in a Z-axis direction and is thus called a fan beam, whereas a cone beam CT (CBCT) uses an X-ray beam that extends along the Z axis as well, and for this reason the X-ray beam is called a cone beam.

Moreover, at present, a type of CBCT apparatus corresponding to a so-called third generation or R/R type in the conventional CT apparatus (that is, an apparatus with only 1 row of sensors) is being studied. In a third-generation CT apparatus, a paired assembly consisting of an X-ray source and a detector scan a subject while revolving around the periphery of the subject.

Figure 9:
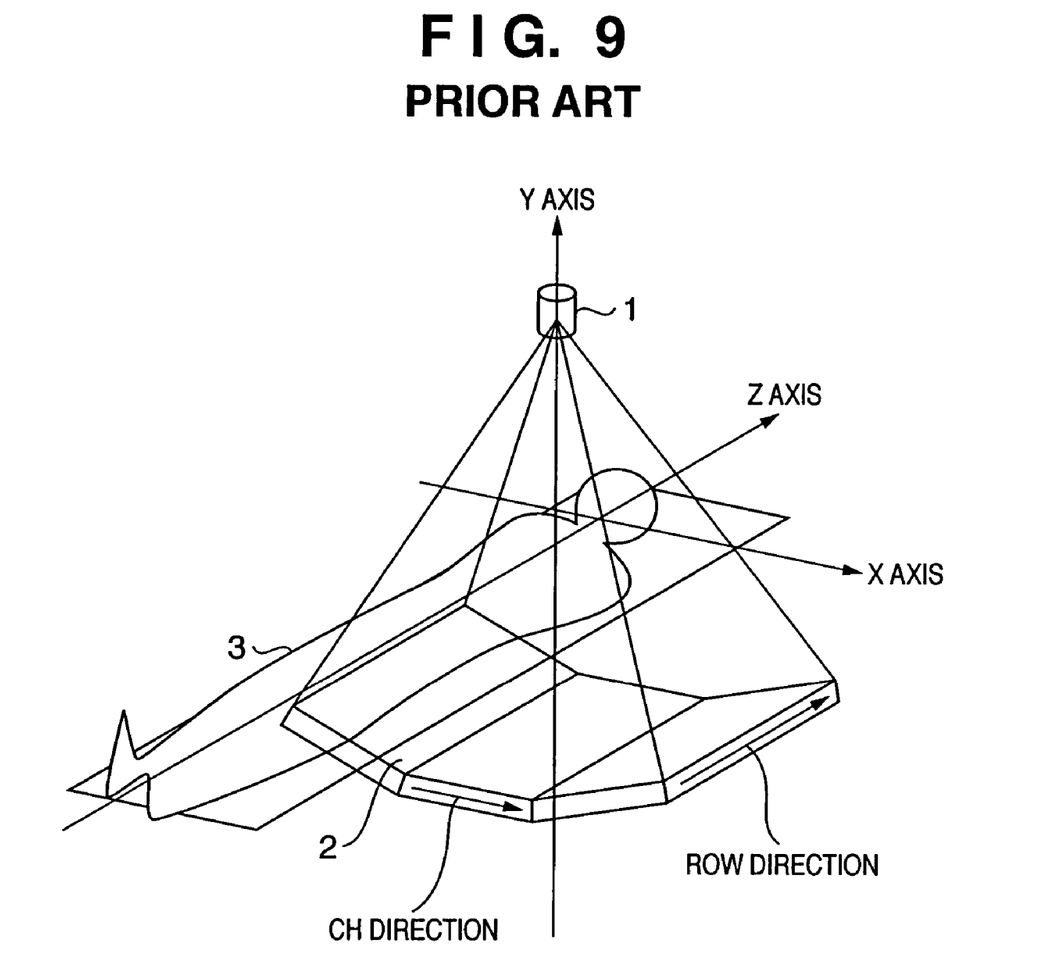
FIG. 9 is a schematic diagram showing an example of the construction of a conventional CBCT apparatus.

FIG. 9 is a schematic diagram showing an example of the construction of a CBCT apparatus. In the diagram, reference numeral 1 denotes an X-ray tube that serves as an X-ray source, 2 denotes an X-ray detector and 3 denotes a subject. The CBCT apparatus shown in FIG. 9 is a third-generation CT apparatus, and takes the Z axis as its axis of rotation as the X-ray tube 1 together with the X-ray detector 2 move around the subject 3 so as to complete scanning of an area of interest in one rotation.

In an ordinary X-ray CT apparatus, in order to carry out sampling in a channel (CH) direction, sensors are aligned in a single line on the X-ray detector in the CH direction, and each individual sensor element is identified by a channel number. By contrast, in the CBCT apparatus shown in FIG. 9, sensors are arrayed in the CH direction as well as in the Z direction (that is, a ROW direction) on the X-ray detector 2. In other words, the X-ray detector 2 in the CBCT apparatus arranges the sensors in a two-dimensional lattice array crossing at right angles.

According to such a CBCT apparatus, by configuring the detector so that the sensors are arranged in two directions like a lattice, in the Z direction (ROW direction) and the CH direction, and at the same time by emitting radiation thickened in the Z direction (that is, in the shape of a cone), projective data of a plurality of rows can be obtained in a single pass (as is disclosed, for example, by Japanese Patent Application Laid-Open No. 2000-107162).

At the same time, in general radiography, flat panel detectors (FPD) using semiconductors have come to be used. FPDs are also adaptable to CT apparatuses, in which case a cone beam CT apparatus can be constructed.

By contrast, there is also a so-called retrofit CT, in which a FPD and a rotating table are mounted on an ordinary X-ray apparatus, the subject is placed on the rotating table and the subject is sensed while being rotated by the rotating table so as to carry out CT scanning with a three-dimensional X-ray geometric system. Such a system has the advantages of realizing computerized tomography inexpensively, using less space than the conventional CT apparatus (as disclosed, for example, in Japanese Patent Application Laid-Open No. 2000-217810).

In a medical radiographic CT apparatus, the pixel values in the image are calibrated based on water so that portions of the subject that absorb radiation like water have a pixel value of zero and portions corresponding to air have a pixel value of −1,000.

In order to reconstruct the image so that the pixels corresponding to a portion equivalent to water read zero and the pixels corresponding to air read −1,000, a preset phantom is radiographed in advance and water calibration is carried out. However, a CBCT apparatus using an FPD requires a long water phantom extending in the direction of the rotation axis for CT (that is, the Z axis), and such water phantom is very heavy. In addition, radiographing of water phantom for the purposes of water calibration is carried out periodically, and therefore handling a large water phantom can be hard and time-consuming.

In addition, with respect to the retrofit CT, no conventional art discloses technique regarding water calibration.

SUMMARY OF THE INVENTION

The present invention has been made in consideration of the above-described situation, and has as its object to facilitate the work for water calibration in a CT system which uses a cone beam of X-rays.

According to the present invention, the foregoing object is attained by providing a radiographic apparatus comprising: a radiation source that emits radiation two-dimensionally; a two-dimensional radiation detector disposed so as to detect radiation emitted from the radiation source; a rotation unit driven so that a subject is relatively rotated with respect to the radiation source and the radiation detector; a detachable water phantom, disposed on the rotation unit, having a size that covers a portion of a detection area of the radiation detector from radiation emitted from the radiation source, the portion extending in the direction perpendicular to the rotation axis for the entire range of the detection area and in the direction of the rotation axis for a part of the range of the detection area; and a calibration unit that performs water calibration of data obtained by radiographing the subject, using data obtained by radiographing the water phantom across the entire detection area while moving a position of the water phantom along the rotation axis of the rotation unit.

Additionally, according to the present invention, the foregoing object is also attained by providing a water calibration method for a radiographic apparatus having a radiation source that emits radiation two-dimensionally, a two-dimensional radiation detector disposed so as to detect radiation emitted from the radiation source, a rotation unit driven so that a subject is relatively rotated with respect to the radiation source and the radiation detector, and a detachable water phantom, disposed on the rotation unit, having a size that covers a portion of a detection area of the radiation detector from radiation emitted from the radiation source, the portion extending in the direction perpendicular to the rotation axis for the entire range of the detection area and in the direction of the rotation axis for a part of the range of the detection area, the water calibration method comprising: acquiring a first data and a second data, the first data obtained by radiographing the water phantom across the entire detection area of the radiation detector while moving a position of the water phantom along the rotation axis of the rotation unit, the second data obtained by detecting radiation emitted from the radiation source and directly incident on the radiation detector; and performing water calibration for a third data obtained by radiographing the subject based on the first data and the second data.

Additionally, according to the present invention, the foregoing object is also attained by providing a water calibration method for a radiographic apparatus having a radiation source that emits radiation two-dimensionally, a two-dimensional radiation detector disposed so as to detect radiation emitted from the radiation source, a radiation quantity detector that measures a quantity of radiation emitted from the radiation source, a rotation unit driven so that a subject is relatively rotated with respect to the radiation source and the radiation detector, and a detachable water phantom, disposed on the rotation unit, having a size that covers a portion of a detection area of the radiation detector from radiation emitted from the radiation source, the portion extending in the direction perpendicular to the rotation axis for the entire range of the detection area and in the direction of the rotation axis for a part of the range of the detection area, the water calibration method comprising: acquiring a first data obtained by radiographing the water phantom across the entire detection area of the radiation detector while moving a position of the water phantom along the axis of rotation; acquiring a second data obtained by measuring the quantity of radiation emitted from the radiation source by the radiation quantity detector; and performing water calibration for a third data obtained by radiographing the subject based on the first data and the second data.

Additionally, according to the present invention, the foregoing object is also attained by providing a radiographic apparatus comprising: a radiation source that emits radiation two-dimensionally; a two-dimensional radiation detector disposed so as to detect radiation emitted from the radiation source; a rotation unit driven so that a subject is relatively rotated with respect to the radiation source and the radiation detector; a unit that extracts a direct radiation portion in each of a plurality of X-ray images obtained by the radiation detector as the rotation unit rotates; and a unit that performs gain correction on the X-ray images based on pixel values of the extracted direct radiation portion.

Other objects, features and advantages of the present invention will be apparent from the following description when taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will be described in detail in accordance with the accompanying drawings.

Figures 1A, 1B:
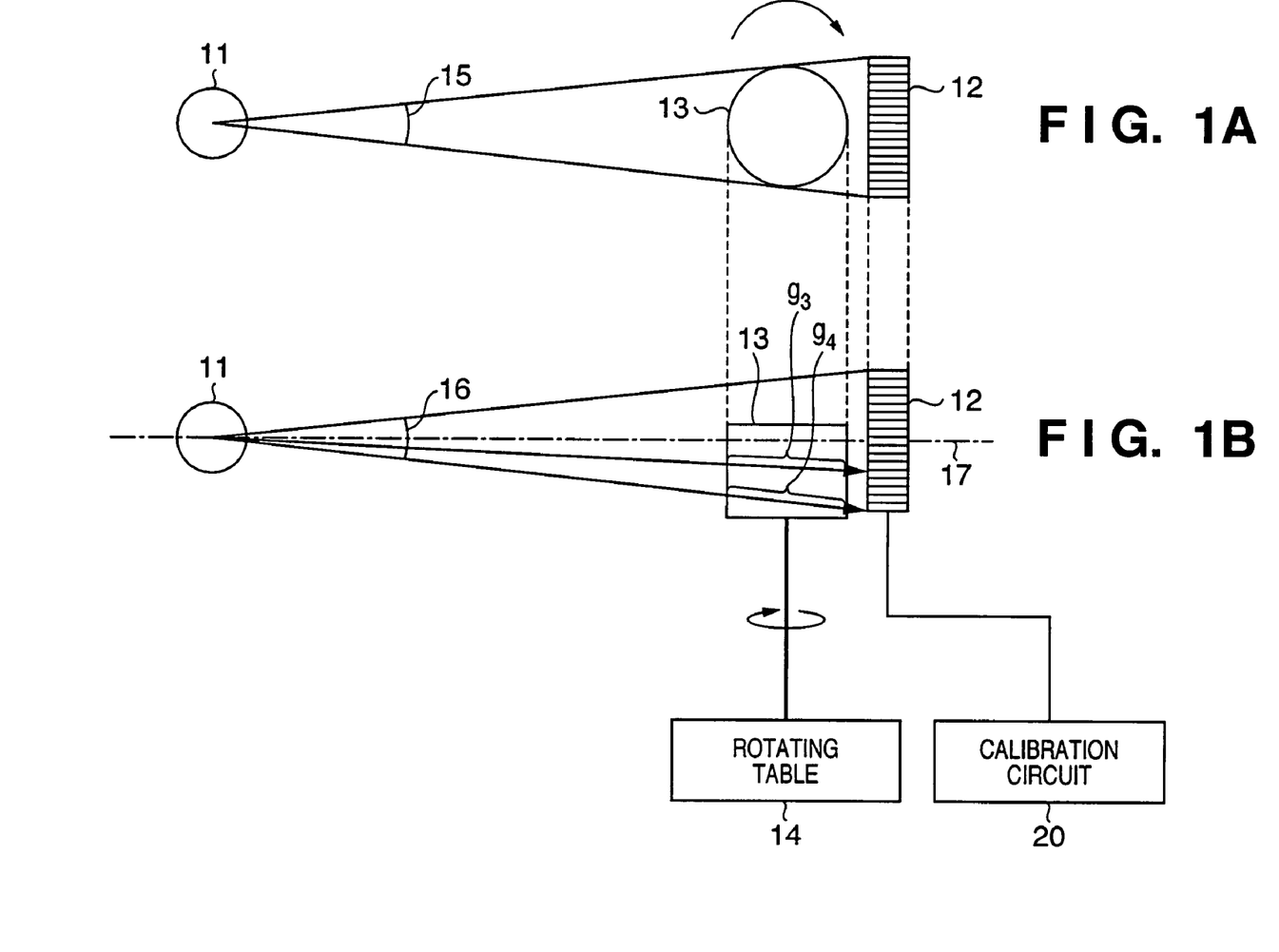
FIGS. 1A and 1B are schematic diagrams showing the construction of a cone beam CT system according to a first embodiment of the present invention, when radiographing a water phantom in a bottom half of a detection area.

FIGS. 1A and 1B are schematic diagrams showing the construction of a cone beam CT system according to a first embodiment of the present invention, when radiographing a water phantom in a bottom half of a detection area. More specifically, FIG. 1A shows a plan view of the system and FIG. 1B shows a lateral view of the system. In FIGS. 1A and 1B, reference numeral 11 denotes an X-ray tube, 12 denotes a two-dimensional detector, 13 denotes a water phantom, 14 denotes a rotating table, 15 denotes an X-ray fan angle, 16 denotes an X-ray cone angle, 17 denotes an optical axis and 20 denotes a calibration circuit.

In the first embodiment, water data is obtained over two passes. In other words, water data is obtained twice, when the water phantom 13 is disposed at a position in a bottom half of the two-dimensional detector 12 and a position in a top half of the two-dimensional detector 12. The water phantom 13 may be radiographed at the bottom half position first or the top half position first, however, in FIGS. 1A and 1B, the water phantom 13 is disposed first in the bottom half of the two-dimensional detector 12 so that the top of the water phantom 13 is slightly above the beam axis 17.

While X-rays are being continuously emitted from the X-ray tube 11, the water phantom 13 is, for example, rotated 360 degrees in the direction indicated by the arrow in FIGS. 1A and 1B by the rotating table 14. The number of pixels in the two-dimensional detector 12 may for example be 1,000×1,000, and the output from the two-dimensional detector 12 is inputted to the calibration circuit 20 connected to the two-dimensional detector 12. The calibration circuit 20 may be either specially configured or implemented by executing the calibration program of the present invention on a general-purpose computer.

Figure 7:
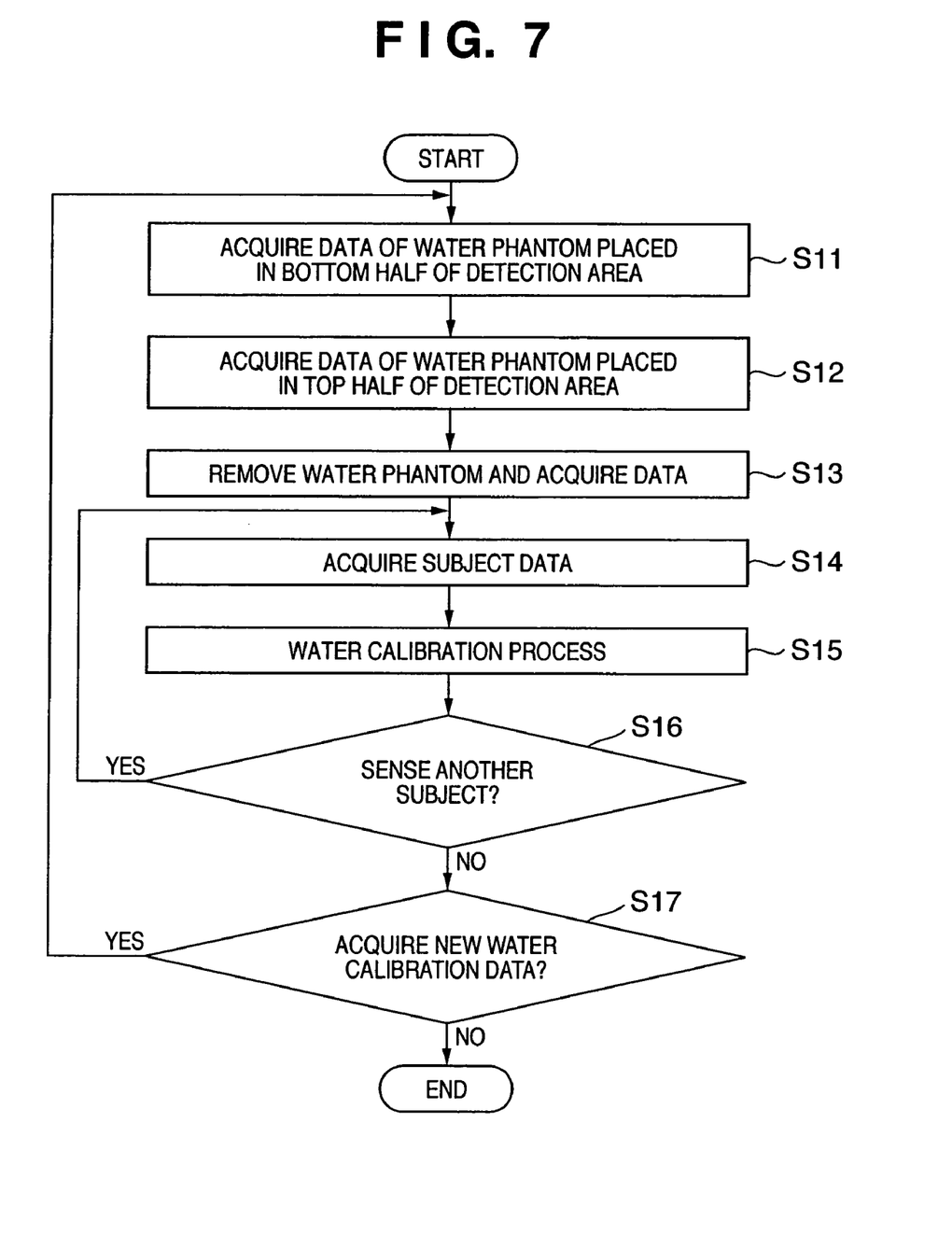
FIG. 7 is a flow chart showing a water calibration procedure in the first embodiment of the present invention.

Next, a description is given of a water calibration method in a CT system having the structure described above with reference to the flow chart shown in FIG. 7. Water calibration is executed by the calibration circuit 20 processing the data output from the detector 12.

Figure 2:
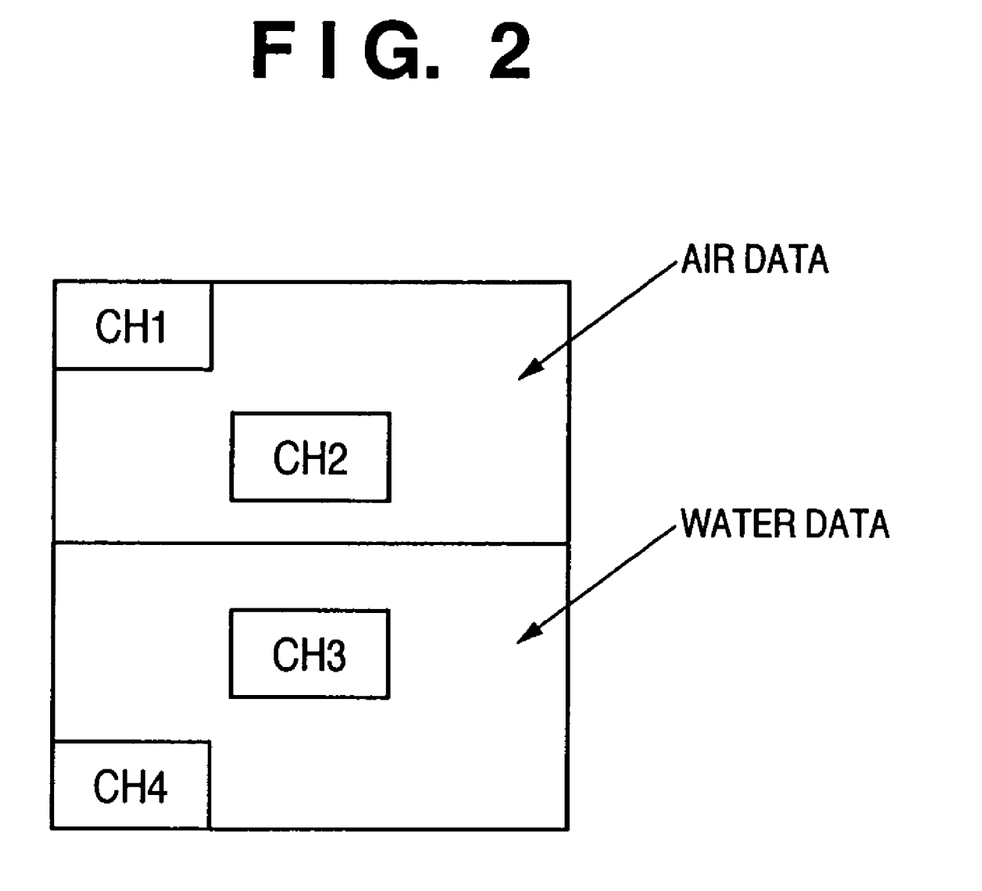
FIG. 2 is a diagram showing conception of data obtained by radiographing the water phantom in the bottom half of the detection area according to the first embodiment of the present invention.

First, in step S11, radiographing is performed in the state shown in FIGS. 1A and 1B, with the data sensed in this state schematically expressed in FIG. 2. Roughly the top half represents air data and the bottom half represents water data. Herein the water calibration method is described using as examples the data portions CH1 through CH4 in the diagram. Since the data portions CH1 to CH4 are obtained from the corresponding areas of the two-dimensional detector 12, the corresponding areas are also referred by CH1 to CH4. In the state shown in FIG. 2, the data portions CH1 and CH2 represent air data and the data portions CH3 and CH4 represent water data. As shown in FIGS. 1A and 1B, if the X-ray attenuation lengths, which are the distances that the X rays travels through the water phantom 13 before reaching the areas CH3 and CH4 in the detector 12, are $g_3$ and $g_4$, respectively, and the counts of X rays which are incident on the areas CH1 to CH4 in the detector 12 are $R_{11}$ to $R_{14}$, then $$R_{11} = C_1 \times I_{S1}$$

$$R_{12} = C_2 \times I_{S1}$$

$$R_{13} = C_3 \times I_{S1} \times \exp(-g_3 \times \mu_w)$$

$$R_{14} = C_4 \times I_{S1} \times \exp(-g_4 \times \mu_w) \quad (1)$$

Here, $I_{S1}$ is the amount of X rays emitted from the X-ray tube 11 when collecting the above-described data, $C_1$ to $C_4$ express the gain of the areas CH1 to CH4, and $\mu_w$ denotes the X-ray absorption coefficient of water.

Figure 3A:
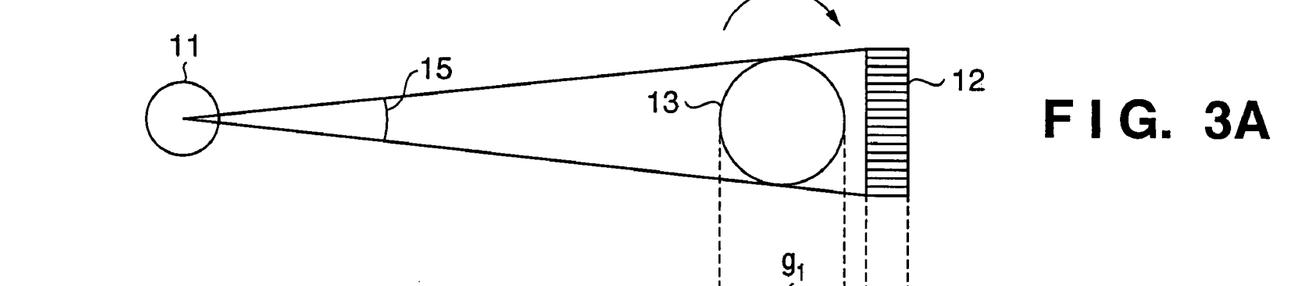
FIGS. 3A and 3B are schematic diagrams showing the construction of the cone beam CT system according to the first embodiment of the present invention, when radiographing the water phantom in a top half of the detection area.
Figure 3B:
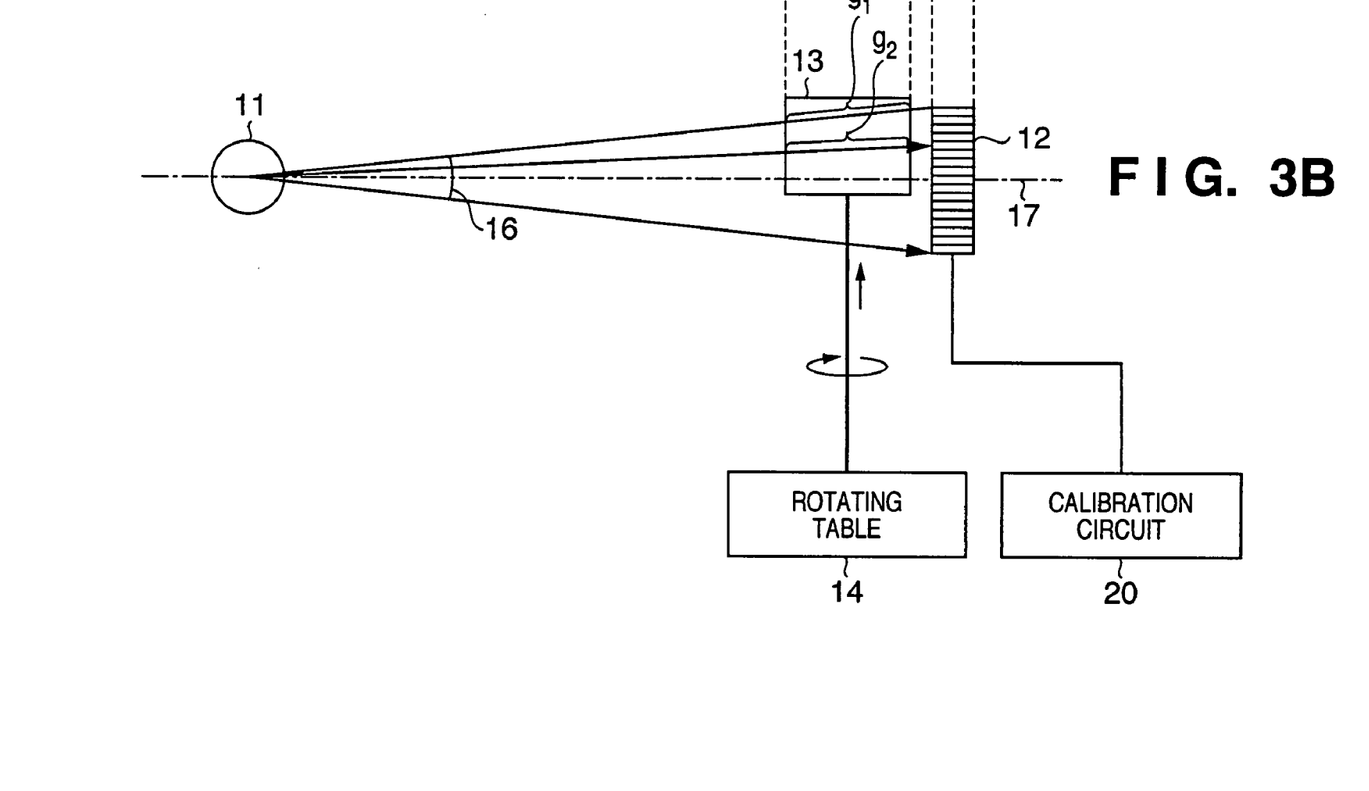
Figure 4:
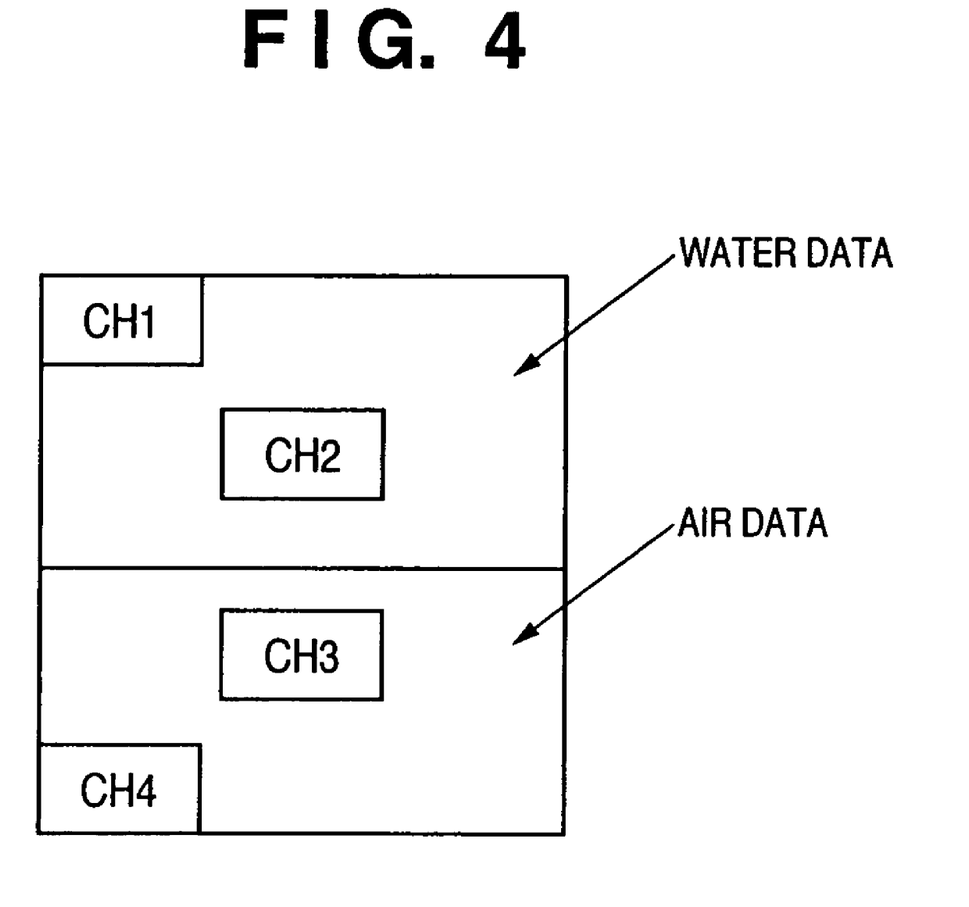
FIG. 4 is a diagram showing conception of data obtained by radiographing the water phantom in the top half of the detection area according to the first embodiment of the present invention.

Next, in step S12, the position of the water phantom 13 is moved up as shown in FIG. 3B and the water phantom is radiographed at this position, that is, collecting water data on the top half of the two-dimensional detector 12 with the CBCT apparatus shown in FIGS. 1A and 1B. FIG. 4 expresses schematically the data sensed in the state shown in FIGS. 3A and 3B. Roughly the top half represents water data and the bottom half represents air data. As shown in FIGS. 3A and 3B, if the X-ray attenuation lengths, which are the distances that the X rays travels through the water phantom 13 before reaching the areas CH1 and CH1, are $g_1$ and $g_2$, respectively, and the counts of X rays which are incident on the areas CH1 to CH4 are $R_{21}$ to $R_{24}$, then $$R_{21} = C_1 \times I_{S2} \times \exp(-g_1 \times \mu_w)$$

$$R_{22} = C_2 \times I_{S2} \times \exp(-g_2 \times \mu_w)$$

$$R_{23} = C_3 \times I_{S2}$$

$$R_{24} = C_4 \times I_{S2} \quad (2)$$

Here, $I_{S2}$ is the amount of X rays emitted from the X-ray tube 11 when collecting the above-described data, $C_1$ to $C_4$ express the gain of the areas CH1 to CH4, and $\mu_w$ denotes the X-ray absorption coefficient of water. Strictly speaking, a supporting column that fixes the water phantom 13 in the top half position is sensed in the air data portion. But this does not affect the water calibration.

Next, in step S13, air data is collected throughout the detection area of the two-dimensional detector 12, in other words, in a state in which there is no water phantom. It should be noted that the order of the processes performed in step S13 as well as steps S11 and S12 described above may be reversed. Although the state of the CBCT system in step S13 is not diagrammed, the counts $R_{01}$ to $R_{04}$ of X rays which are incident on the areas CH1 to CH4 become as follows:

$$R_{01} = C_1 \times I_{S0}$$

$$R_{02} = C_2 \times I_{S0}$$

$$R_{03} = C_3 \times I_{S0}$$

$$R_{04} = C_4 \times I_{S0} \quad (3)$$

Here, $I_{S0}$ is the amount of X rays emitted from the X-ray tube 11 when collecting the above-described data, and $C_1$ to $C_4$ express the gain of the areas CH1 to CH4. The data obtained in the steps S11–S13 described above (hereinafter "water calibration data") is then stored in a memory, not shown, of the calibration circuit 20.

Figure 5A:
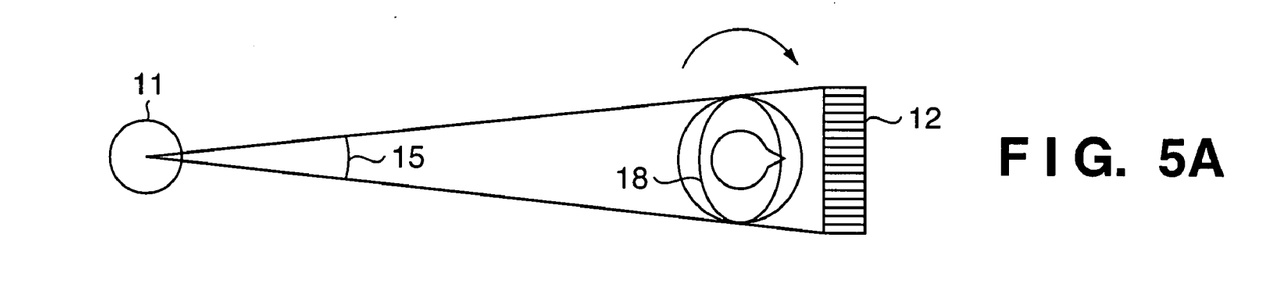
FIGS. 5A and 5B are schematic diagrams showing the construction of the cone beam CT system according to the first embodiment of the present invention, when radiographing an subject.
Figure 5B:
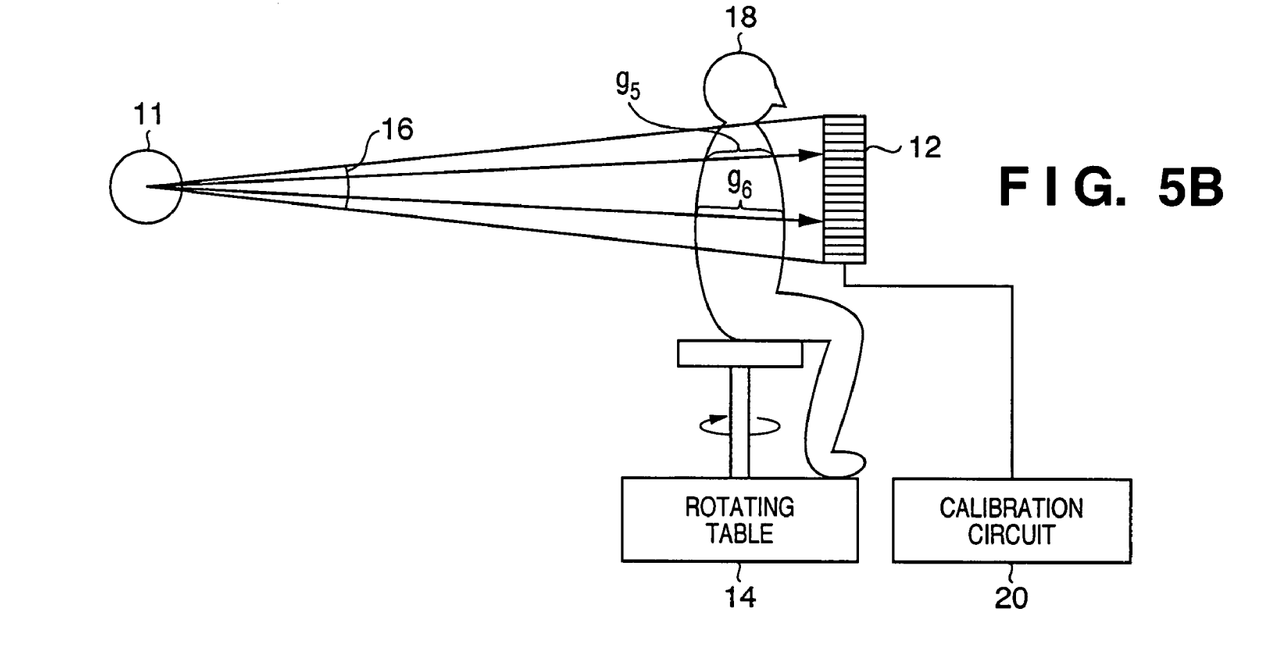
Figure 6:
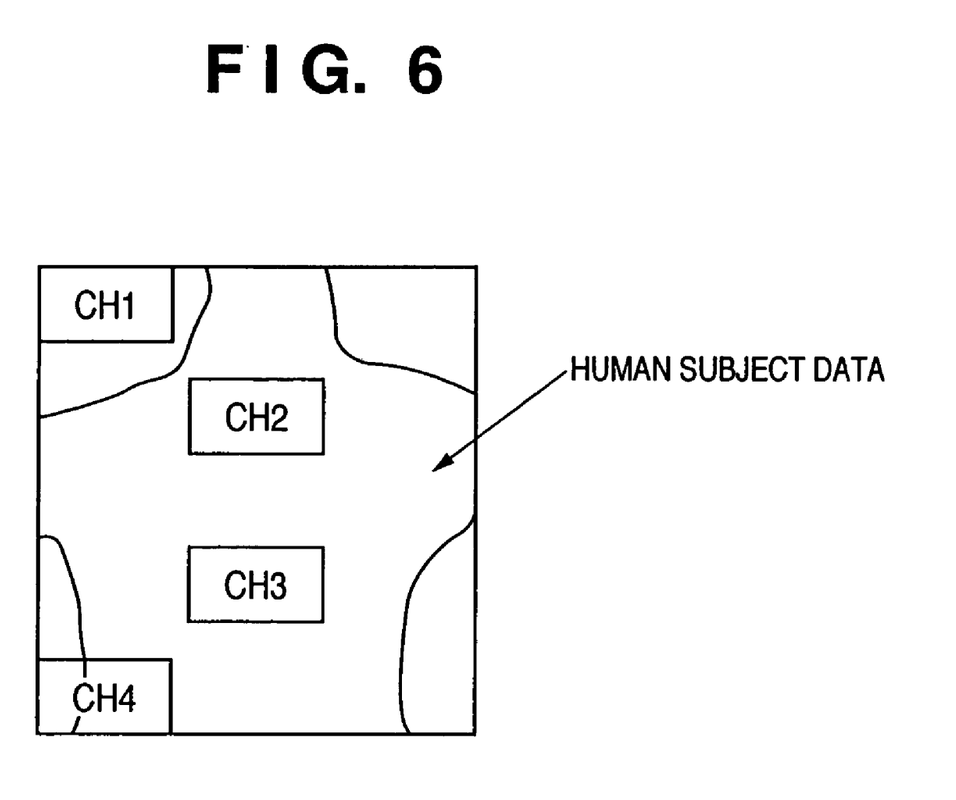
FIG. 6 is a diagram showing conception of data obtained by radiographing the subject according to the first embodiment of the present invention.

Next, in step S14, the subject is radiographed using the system as shown in FIGS. 1A and 1B to obtain subject data. FIGS. 5A and 5B show a state in which the subject 18 is being radiographed, in which FIG. 5A shows a top view of the system and FIG. 5B shows a lateral view of the system. FIG. 6 shows an example of the data obtained at a particular time with this system. If the amount of X rays emitted from the X-ray tube 11 when collecting the data of the subject is $I_s$ and $\mu$ denotes the X-ray absorption coefficient of the subject 18, then $$R_1 = C_1 \times I_S$$

$$R_2 = C_2 \times I_S \times \exp(-g_5 \times \mu)$$

$$R_3 = C_3 \times I_S \times \exp(-g_6 \times \mu) \quad (4)$$

In step S15, water calibration is performed on the subject data obtained in step S14 using the water calibration data obtained in steps S11–S13. Specifically, by removing any difference in gain among the pixels from the data $R_2$ and $R_3$ of the areas CH2 and CH3 shown in equation (4) and obtaining the difference between the X-ray absorption coefficient of the water and that of the subject 18, water calibration can be accomplished. Thus, from equations (2), (3) and (4) above, $$\exp(-g_2 \times \mu_w) = \frac{R_{22} \times R_{04}}{R_{24} \times R_{02}} \quad (5)$$

$$\exp(-g_5 \times \mu) = \frac{R_2 \times R_{01}}{R_1 \times R_{02}}$$

From equation (5), data expressing the difference with the X-ray absorption coefficient of data portion CH2 can be obtained:

$$(g_5 \times \mu - g_2 \times \mu_w) = \ln\left(\frac{R_{22} \times R_{04} \times R_1}{R_{24} \times R_2 \times R_{01}}\right) \quad (6)$$

Similarly, the following equation (7) can be obtained using equations (1), (3) and (4):

$$(g_6 \times \mu - g_3 \times \mu_w) = \ln\left(\frac{R_{13} \times R_1}{R_{11} \times R_3}\right) \quad (7)$$

For those data portions not described above as well, the difference with the water data can be obtained in the same way as that used to deduce equations (6) and (7) above. As is clear from the equations, if the water phantom 13 is sensed as the subject, the calibrated CT values of the subject become zero. In order to set the CT values when air is radiographed to −1,000, the image is reconstructed by multiplying the values obtained in equation (6) or equation (7) by an appropriate constant.

In step S16 in FIG. 7, it is ascertained whether or not another subject is to be radiographed, and if so (that is, YES in step S16), the process returns to step S14 and the water calibration procedure described above is repeated for the sensed subject. If no new subject is to be sensed (NO in step S16), then the process proceeds to step S17, where it is ascertained whether or not new water calibration data is to be obtained, and if so (YES in step S17), the process returns to step S11, otherwise, the processing ends.

It should be noted that, in the first embodiment of the present invention described above, it is necessary that X rays are directly incident on any of the areas (CH) of the two-dimentional detector 12 during sensing of the subject 18. This direct radiation is detected in the area CH1 in the first embodiment, but generally can be searched for by processing the image. In searching the area of the direct radiation, a subject area is first extracted, then a portion of the detector 12 farthest from the subject area is determined. It is preferable that the determined portion includes a plurality of pixels. In extracting the subject area, a threshold for binarization is decided, data obtained by radiographing the subject is binarized using the threshold, the binarized data is grouped by labeling process, the group having the largest area is extracted, and the area is determined as the subject area. Other than above, a variety of methods of defining the subject area by processing an image are commonly known, and any method may be employed for this purpose. Alternatively, the direct radiation area may be empirically chosen from the four corner portions of the two-dimensional detector 12 based on the portion of the human body to be radiographed and the rotation angle of the table 14. For example, when performing CT for the chest, it may be decided based on the knowledge of the shape of the human body that either of the bottom corner portions of the detector 12 is suitable for detecting the direct radiation in radiographing the chest from the front with respect to a back support board and that either of the top corner portions is suitable in radiographing the chest from the side with respect to the back support board.

As described above, the first embodiment of the present invention enables overall water calibration for a cone beam CT apparatus to be performed using a water phantom that does not completely cover the entire FPD or other such two-dimensional detector, thus facilitating the work of water calibration.

Second Embodiment

A description will now be given of a second embodiment of the present invention.

A drawback of the first embodiment described above is that it is necessary to direct X rays directly into one of the areas (CH) of the two-dimensional detector 12 during radiographing a subject. In addition, there is a possibility of backscatter. As a method of avoiding these drawbacks, a reference detector may be provided on a radiation window as has been conventionally done.

Figure 8A:
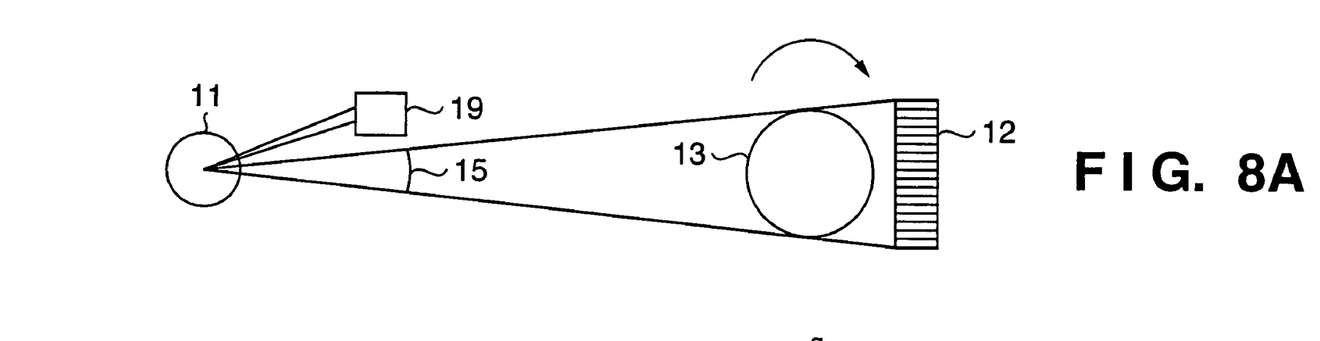
FIGS. 8A and 8B are schematic diagrams showing the construction of a cone beam CT system according to a second embodiment of the present invention.
Figure 8B:
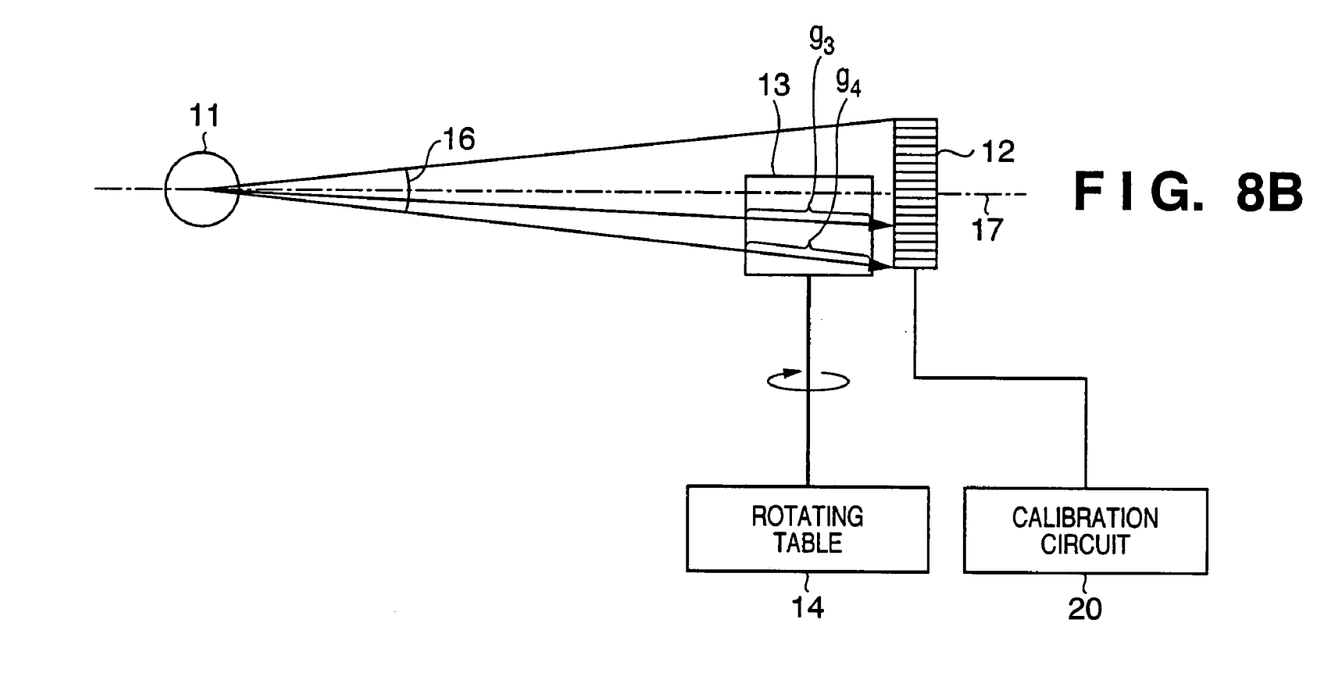

FIGS. 8A and 8B show an example of the disposition of an upright patient rotation-type CT system including a reference detector 19 of the second embodiment of the present invention. It should be noted that the same reference numerals are used for structures that are identical to those in FIGS. 1A and 1B, and a redundant description thereof is omitted here. The reference detector 19 integrates the radiation quantity of X rays over the same period of time as the X rays are incident on the two-dimensional detector 12, and the radiation quantity detected by the reference detector 19 and the radiation quantity detected by the detector 12 has linear relation. That is, X-ray fluctuation within the integral time can be cancelled out.

The water calibration method used when the configuration of the CT system includes the reference detector 19 is described below. If the reference channel CH input is described as Rr, then, in the second embodiment, the data collected in place of equations (1), (2), (3) and (4) of the first embodiment, may be expressed as $$R_{11} = C_1 \times I_{S1}$$

$$R_{12} = C_2 \times I_{S1}$$

$$R_{13} = C_3 \times I_{S1} \times \exp(-g_3 \times \mu_w)$$

$$R_{14} = C_4 \times I_{S1} \times \exp(-g_4 \times \mu_w)$$

$$R_{1r} = C_r \times I_{S1} \quad (8)$$

$$R_{21} = C_1 \times I_{S2} \times \exp(-g_1 \times \mu_w)$$

$$R_{22} = C_2 \times I_{S2} \times \exp(-g_2 \times \mu_w)$$

$$R_{23} = C_3 \times I_{S2}$$

$$R_{24} = C_4 \times I_{S2}$$

$$R_{2r} = C_r \times I_{S2} \quad (9)$$

$$R_1 = C_1 \times I_S$$

$$R_2 = C_2 \times I_S \times \exp(-g_5 \times \mu)$$

$$R_3 = C_3 \times I_S \times \exp(-g_6 \times \mu)$$

$$R_r = C_r \times I_S \quad (10)$$

Using equations (8) through (10) to obtain the equivalents of equations (6) and (7) in the second embodiment yields the following:

$$(g_5 \times \mu - g_2 \times \mu_w) = \ln\left(\frac{R_{22} \times R_r}{R_2 \times R_{2r}}\right) \quad (11)$$

$$(g_6 \times \mu - g_3 \times \mu_w) = \ln\left(\frac{R_{13} \times R_r}{R_3 \times R_{1r}}\right) \quad (12)$$

It should be noted that, as described above, it is necessary to direct X rays directly into one of the areas (CH) of the two-dimensional detector 12 during image sensing in the first embodiment. By contrast, because the CT system according to the second embodiment uses a reference detector 19, it is possible to use a water phantom that entirely covers the two-dimensional detector 12. In that case, sensing of the water phantom is completed in one pass. At the same time, the advantage of using a water phantom 13 that covers approximately half the two-dimensional detector 12 as in the first embodiment is that the mass of the phantom can be reduced, thus easing handling.

In addition, it goes without saying that, although the first and second embodiments are described above using an upright patient rotation-type CT system as an example, the present invention is not limited to such an upright patient rotation-type CT system, and thus, alternatively, as shown in FIG. 9, the present invention can also be adapted to a type of CT apparatus in which the subject is stationary and the X-ray tube and X-ray detector are rotated.

In addition, as can be appreciated by those of ordinary skill in the art, although the first and second embodiments are described above using the water phantom 13 that covers approximately half the detector 12, the present invention is not limited thereto. Alternatively, a water phantom of a size to cover less than half of the detection area of the detector 12, for example one third or one fourth of such detection area, may be used, and in that case, the number of times of radiographing such the water phantom is increased in order to obtain water data. Furthermore, a water phantom may be used that is of a size that leaves at least one direct radiation detection area uncovered, for example, of a size that is two thirds the size of the detection area of the detector 12.

As many apparently widely different embodiments of the present invention can be made without departing from the spirit and scope thereof, it is to be understood that the invention is not limited to the specific embodiments thereof except as defined in the appended claims.

What is claimed is:

1. A radiographic apparatus comprising:
   a X-ray radiation source that emits X-ray radiation;
   a X-ray radiation detector in which detection elements detect X-ray radiation are arranged as a two-dimensional array;
   a rotation unit, capable of changing its height, driven so that a subject is relatively rotated with respect to said X-ray radiation source and said X-ray radiation detector;
   a detachable water phantom, disposed on said rotation unit, having a size that covers at least a row of said detection elements from radiation emitted from said X-ray radiation source;
   a moving unit that moves said water phantom along a rotation axis of said rotation unit so as to radiograph said water phantom across the entire detection elements; and
   a calibration unit that performs water calibration of data obtained by radiographing the subject, using data obtained by radiographing said water phantom across the entire detection elements.

2. The radiographic apparatus according to claim 1, wherein said calibration unit performs water calibration further using data obtained by detecting X-ray radiation emitted from said X-ray radiation source and directly incident on said X-ray radiation detector.

3. The radiographic apparatus according to claim 1, further comprising a radiation quantity detector that measures a quantity of X-ray radiation emitted from said X-ray radiation source,
   wherein said calibration unit performs water calibration using data on the quantity of X-ray radiation measured by said radiation quantity detector.

4. The radiographic apparatus according to claim 1, wherein said rotation unit rotates the subject with respect to said X-ray radiation source and said X-ray radiation detector.

5. The radiographic apparatus according to claim 1, wherein said rotation unit rotates said X-ray radiation source and said X-ray radiation detector with respect to the subject.

6. The radiographic apparatus according to claim 1, wherein said water phantom has a size that covers substantially half of said detection elements of said X-ray radiation detector along the rotation axis of said rotation unit from X-ray radiation emitted from said X-ray radiation source.

7. A radiographic apparatus comprising:
   a X-ray radiation source that emits X-ray radiation
   a two-dimensional X-ray radiation detector disposed so as to detect X-ray radiation emitted from said X-ray radiation source;
   a rotation unit driven so that a subject is relatively rotated with respect to said X-ray radiation source and said X-ray radiation detector;
   an extraction unit that extracts data corresponding to a direct X-ray radiation portion where the X-ray radiation has not passed through the subject from data obtained by sensing the subject by said x-ray radiation detector;
   a gain correction unit that performs gain correction on the data based on pixel values of the extracted direct X-ray radiation portion and
   a reconfiguration unit that obtains a reconfigured data on the basis of the gain-corrected data.

8. A radiographing method comprising:
   placing a water phantom along a rotation axis of a rotation unit which is for rotating a subject with respect to a X-ray radiation source and a two-dimensional X-ray radiation detector so as to cover a part of the X-ray radiation detector;
   emitting X-ray radiation toward the water phantom;
   converting the X-ray radiation emitted toward the water phantom into a plurality of data by the X-ray radiation detector;
   extracting data from the plurality of data corresponding to a direct X-ray radiation portion of the X-ray radiation detector where X-ray radiation directed is incident without passing through the water phantom; and
   calibrating the plurality of data using the extracted data.

* * * * *